US006238378B1

(12) United States Patent
Perez

(10) Patent No.: US 6,238,378 B1
(45) Date of Patent: May 29, 2001

(54) WASTE EVACUATION SYSTEM

(76) Inventor: Francisco Perez, 717 W. Riordan Rd., Flagstaff, AZ (US) 86001

( * ) Notice: Subject to any disclaimer, the term of this patent is extended or adjusted under 35 U.S.C. 154(b) by 0 days.

(21) Appl. No.: 09/058,472

(22) Filed: Apr. 10, 1998

Related U.S. Application Data

(60) Provisional application No. 60/043,529, filed on Apr. 11, 1997.

(51) Int. Cl.$^7$ ..................................................... A61M 1/00
(52) U.S. Cl. ........................................... 604/317; 604/348
(58) Field of Search ..................................... 604/317, 345, 604/322, 349, 119, 320; 428/317.1; 528/80

(56) References Cited

U.S. PATENT DOCUMENTS

| 1,399,676 | * | 12/1921 | Waggoner | 128/276 |
|---|---|---|---|---|
| 2,223,566 | * | 12/1940 | Koch | 604/343 |
| 2,331,226 | * | 10/1943 | Pritchard | 604/343 |
| 2,366,059 | * | 12/1944 | Schunk | 604/343 |
| 2,491,799 | * | 12/1949 | Clarke | 128/276 |
| 2,778,362 | * | 1/1957 | Pollock et al. | 128/276 |
| 3,626,941 | * | 12/1971 | Webb | 128/283 |
| 3,989,046 | * | 11/1976 | Pannier, Jr. et al. | 128/276 |
| 4,218,781 | * | 8/1980 | Lieberman | 2/247 |
| 4,256,109 | * | 3/1981 | Nichols | 128/276 |
| 4,281,655 | * | 8/1981 | Terauchi | 128/278 |
| 4,439,599 | * | 3/1984 | Watanabe et al. | 528/80 |
| 4,465,485 | * | 8/1984 | Kashmer et al. | 604/320 |
| 4,533,355 | * | 8/1985 | Fair | 604/345 |
| 4,592,750 | * | 6/1986 | Kay | 604/337 |
| 4,596,566 | * | 6/1986 | Kay | 604/343 |
| 4,747,166 | * | 5/1988 | Kuntz | 4/144.1 |
| 4,888,006 | * | 12/1989 | Beaupied | 604/345 |
| 4,907,298 | * | 3/1990 | Lisowski | 2/212 |
| 5,048,122 | * | 9/1991 | Prieur | 2/69 |
| 5,135,520 | * | 8/1992 | Beaupied | 604/345 |
| 5,149,325 | * | 9/1992 | Telang et al. | 604/119 |
| 5,300,052 | * | 4/1994 | Kubo | 604/349 |
| 5,584,826 | * | 12/1996 | Faenger et al. | 604/322 |
| 5,693,412 | * | 12/1997 | Walters | 428/317.1 |
| 5,935,878 | * | 8/1999 | Glasser | 442/30 |

\* cited by examiner

Primary Examiner—Kim M. Lewis
(74) Attorney, Agent, or Firm—Royston, Rayzor, Vickery, Novak & Druce, L.L.P.

(57) ABSTRACT

A bodily waste evacuation system, particularly adapted for use with an immobile patient, generally comprises a pair of shorts, or other like undergarment-type apparel, and a collection and storage unit in operable and fluid communication with the shorts. The shorts are provided with a plurality of connecting tubes for the removal of bodily wastes and a plurality of connecting tubes for the supply of cleansing liquid and drying air. The collection and storage unit generally comprises a plurality of removable chambers. Each chamber is in fluid communication with the shorts via the connecting tubes. A plurality of separate chambers are utilized for storing waste, liquid waste, and the cleansing fluids. A vacuum operated waste collection system is included, as well as a source of drying air to be diffused upon the patient. There is also a means for heating the cleansing liquid and/or the drying air so that it is assured to be at a desired temperature for patient comfort and increased drying efficacy. A pump is included for supplying the cleansing liquid to the patient's rectal and/or genital areas. A microprocessor based timing and control system is utilized in the automation of the invention's operation. Those components exclusive of the part and connective tubing portions may be housed in a unified base described as the collection and storage unit.

35 Claims, 5 Drawing Sheets

WASTE EVACUATION SYSTEM

RELATED PATENT APPLICATION

This patent application claims priority to United States Provisional application Ser. No. 60/043,529 filed Apr. 11, 1997 entitled WASTE EVACUATION SYSTEM pursuant to 35 U.S.C. 119(e). By this reference the entire disclosure, including the drawings, of Provisional application Ser. No. 60/043,529 is incorporated herein.

FIELD OF THE INVENTION

The present invention relates to sanitary apparel adapted for automated removal of bodily wastes from non-ambulatory, immobile or substantially immobile patients. More particularly, the invention pertains to an apparatus and method for automatically detecting the presence of solid and/or liquid waste that has been excreted by a patient, activating a vacuum removal system, cleansing the patient with warm water or other conditioned fluid, and then drying the patient with diffused air.

BACKGROUND OF THE INVENTION

Many patients who are committed to bed for short or extended periods of time are unable to make use of ordinary restroom facilities. This is particularly true for persons that are comatose or unconscious for longer periods of time. All of these patients are often diapered and are typically wholly reliant upon family members or other care givers for assistance with their basic sanitary needs, including relieving themselves.

In these situations, it is not only important that the waste be removed from about the patient, but it must be removed promptly so that it does not foster other health problems such as rashes and infection. To assure the these undesirable results are minimized, waste that does contact the patient must be washed away and the skin dried. These cleansing steps help minimize skin irritation and infection of the patient.

In addition to the health concerns associated with the patient's inability to deal with their own waste, there are also more aesthetic concerns such as cleanliness of clothing and bedding, and odors that are often associated therewith. Still further, the patient may also suffer emotional discomfort and other embarrassment because such situations cause their dependence on others for such intimate matters associated with their bodily functions.

It is therefore a fundamental object of the present invention to overcome the limitations of the prior art by providing a method and apparatus by which a patient may be kept clean, odors minimized, and embarrassing or uncomfortable situations reduced for the patient and care giver, alike.

It is a further object to provide an apparatus easily affixed about a patient in an adjustable manner and which is adaptable to a wide variety of patients, as well as being flexible in use. The invention should also be comfortable against a patient's skin and not cause irritation or prevent the complete removal of waste therefrom.

Yet another object of the present invention is to provide a system that is small, lightweight, and portable for use in hospital, residential, and less refined and protected environments.

In view of the above described deficiencies associated with the use of known waste evacuation systems, the present invention has been developed to alleviate these drawbacks and provide further benefits to the user. These enhancements and benefits are described in greater detail hereinbelow with respect to several alternative embodiments of the present invention.

SUMMARY OF THE INVENTION

The present invention in its several disclosed embodiments alleviates the drawbacks described above with respect to waste evacuation systems and incorporates several additionally beneficial features.

The beneficial effects described above apply generally to each of the exemplary devices and mechanisms disclosed herein of the waste evacuation system. The specific structures through which these benefits are delivered will be described in detail hereinbelow.

This invention finds primary application in the care and attendance of patients confined to a bed for extended periods, and especially unconscious patients, regardless of the duration of the disability. This may include patients in various conditions, but definitely includes those patients that are comatose, or those that have suffer head injuries and suffer from deep concussions that cause them to be unconscious or semi-conscious for long periods of time during which they are confined to a bed. Obviously, these patients continue to produce waste that can cause severe heath risks if not promptly removed. This invention provides a means by which this removal can be accomplished promptly, and without the need for personal attendance from another person.

The benefits associated with the present invention stem from the fact that waste is essentially intercepted by the apparatus and immediately diverted away from the patient at the time it is excreted. This prevents the waste from being spread about the patient and soiling both the patient and the immediate surroundings, including clothing, bedding and other medical devices and machinery being used upon the patient. This is particularly important with regard to clothing and bedding which must be changed, not merely cleaned in-place when a patient soils them. By using the waste removal system of the present invention, there will also be a dramatic downstream environmental benefit through laundering reductions.

Because the invention negates the requirement of another person to attend to the removal of the patient's waste, medical personnel are freed for more productive duties that require their attention and expertise. In this same vain, the present invention positively affects care givers in that it eliminates one of their more offensive duties; the same being the removal of human waste and the subsequent cleansing of the patient's body that is presently required. More importantly, it minimizes contact between the care provider and the human waste. This is important because such waste may be infectious and potentially harmful or lethal to the contacting person.

It is important to appreciate that utilization of the waste removal system of the present invention is not limited to hospital settings. It may find similar application in convalescence homes, nursing homes, physical therapy facilities, institutions, and private residences.

It is contemplated that the invention may be constructed in at least two embodiments. One embodiment is of a more permanent nature and is expected to remain in a particular facility, even though it is portable to the extent that it may be moved from room-to-room and patient-to-patient. A second embodiment is self-contained in that it carries its own powering system in the form of a battery pack. Furthermore, because of its compact and lightweight construction, the entire unit of this embodiment may be manually carried between different locations. Because of its entirely self-contained nature, it finds particular utility in remote locations and in those situations where conventional power may not be readily available. These situations may be experienced in lesser developed areas and in emergency and rescue circumstances.

It is expected that the mobile unit will find particular utility in lesser and under developed countries where medical facilities and equipment are greatly needed, but often unavailable or unsupportable because of local conditions. By being self-contained, the present invention performs equally well in the most industrialized cities and the most remote out-backs.

In accordance with those objects outlined herein above, the present invention generally comprises a bodily waste evacuation system generally comprising a pair of specially adapted, flexibly applied shorts having a plurality of removably attachable connecting tubes in operable and fluid communication with a urine and feces collection and storage unit. The unit generally allows for the separate extraction of urine and feces, the cleansing of the patient after urination or a bowel movement, and the drying of the patient after these processes. As facets of the automatic characteristics of the invention, timing and control means are provided to ensure maximally efficient operation of the apparatus of the invention and to ensure effective cleansing of the patient.

BRIEF DESCRIPTION OF THE DRAWINGS

Although the scope of the present invention is much broader than any particular embodiment that may be described herein, a detailed description of the preferred embodiment follows, together with illustrative figures, wherein like reference numerals refer to like components, and wherein.

DETAILED DESCRIPTION OF THE INVENTION

Figure 1:
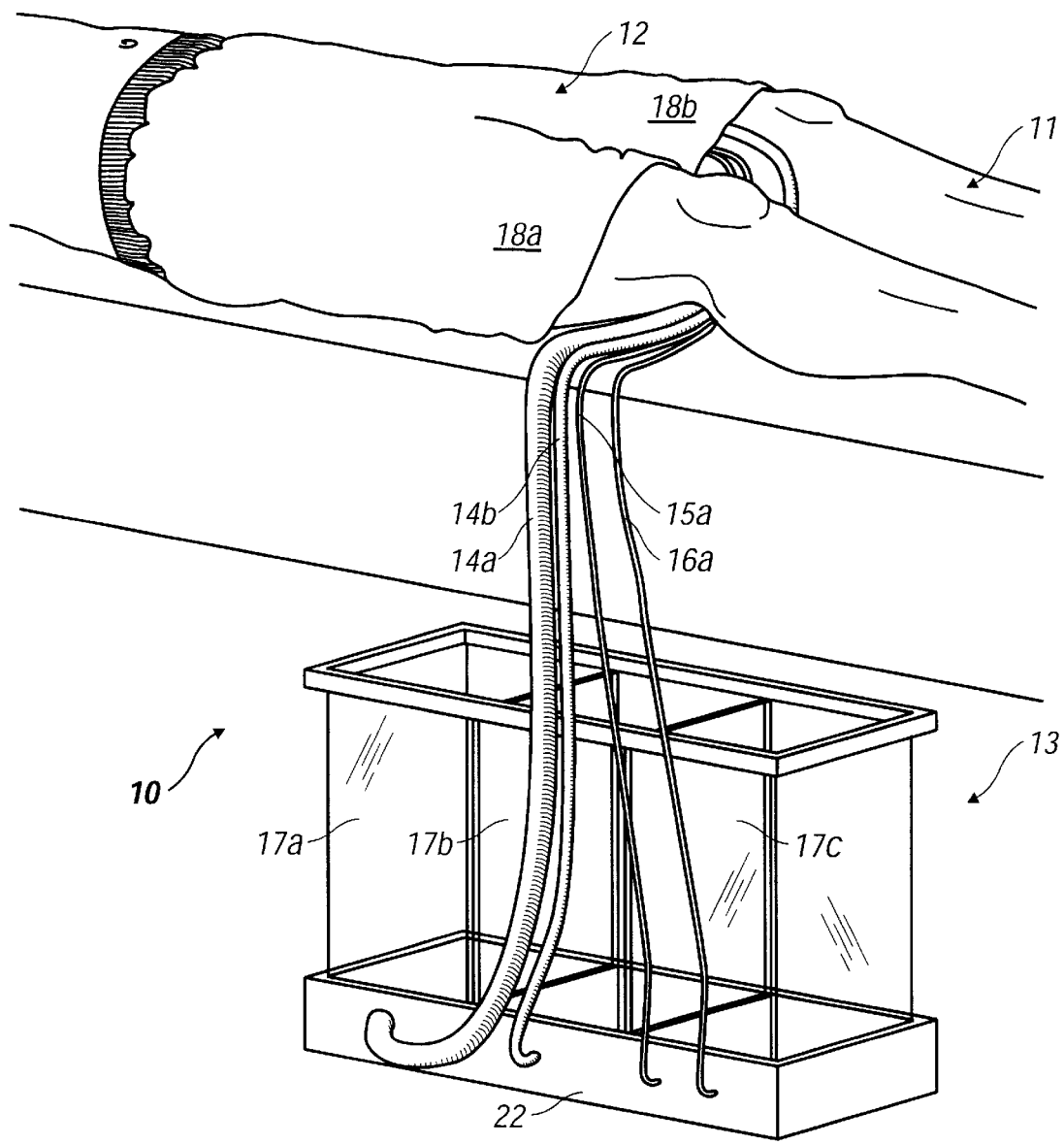
FIG. 1 is a perspective view of the preferred embodiment of the present invention, a bodily waste evacuation system 10 is operably associated with a patient 11 and broadly comprises a pair of specially adapted shorts 12 in operable and fluid communication with a collection and storage unit 13.

Although those of ordinary skill in the art will readily recognize many alternative embodiments of the presently disclosed invention, especially in light of the illustrations provided herein, this detailed description is exemplary of the preferred embodiment of the present invention, the scope of which is limited only by the claims drawn thereto. The preferred embodiment of the present invention, a bodily waste evacuation system 10 particularly adapted for use with an immobile patient 11, generally comprises a pair of shorts 12, or other like undergarment-type apparel, and a distribution, collection and storage unit 13 in operable and fluid communication with the shorts 12. According to the preferred embodiment of the present invention, the shorts 12 are provided with a plurality of connecting tubes 14 for the removal of bodily wastes and a plurality of connecting tubes 15, 16 for the supply of cleansing liquid and drying air. The collection and storage unit 13 generally comprises a plurality of removable chambers 17, in fluid communication with the shorts 12 via the connecting tubes 14, 15, 16, for separate storage of primarily solid wastes, liquid wastes, and cleansing fluid; a vacuum operated waste collection system; a source of drying air; means for heating the cleansing liquid and/or drying air to a desired temperature for patient comfort and increased drying efficacy; a pump for supplying the cleansing liquid to the patient's rectal and/or genital areas; and a microprocessor based timing and control system. All of these latter features may be housed in the base 22 of the collection and storage unit 13.

Figure 2:
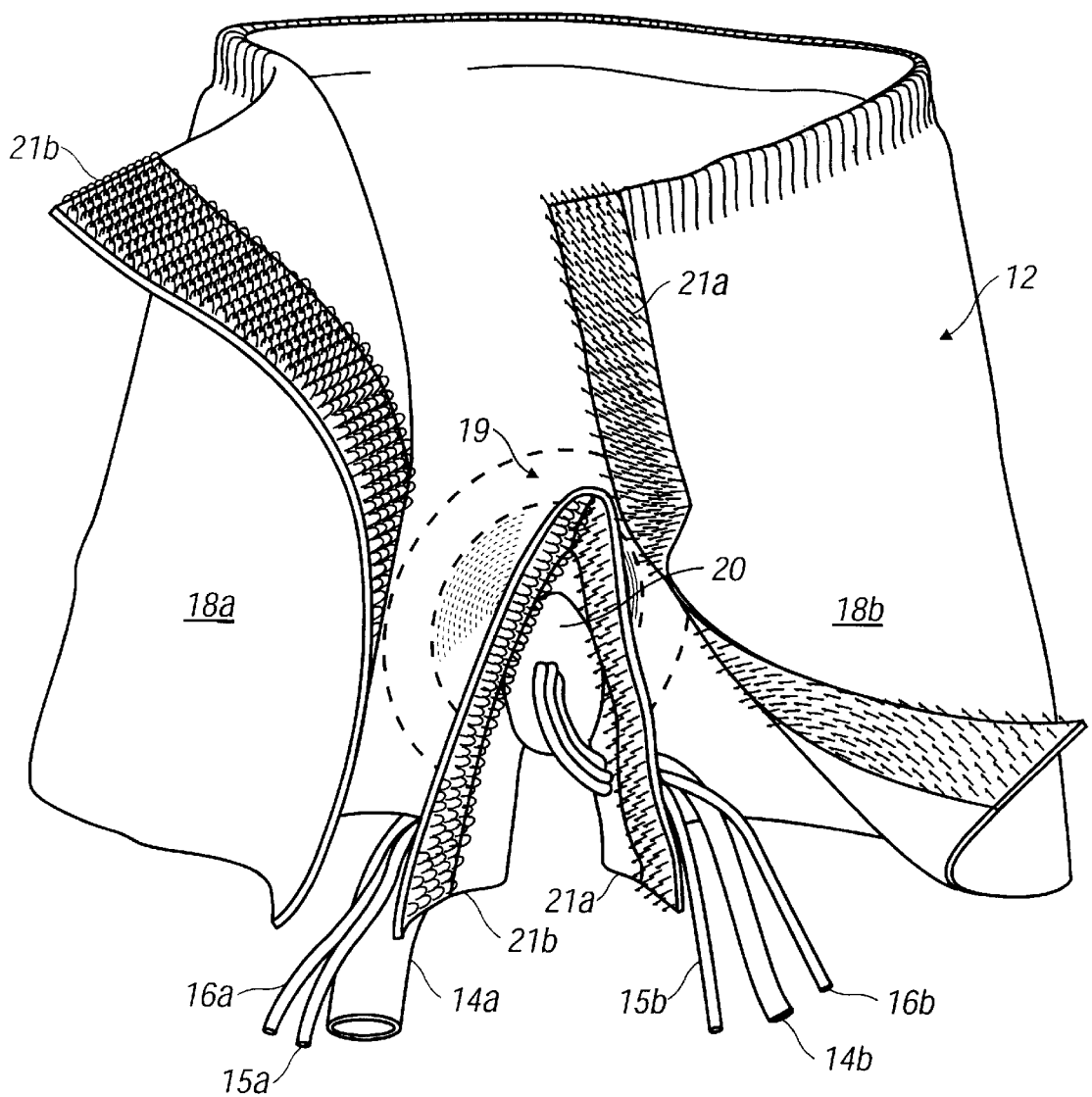
FIG. 2 is a front, perspective view of the specially adapted shorts 12 of the preferred embodiment of the present invention in their open condition.
Figure 4:
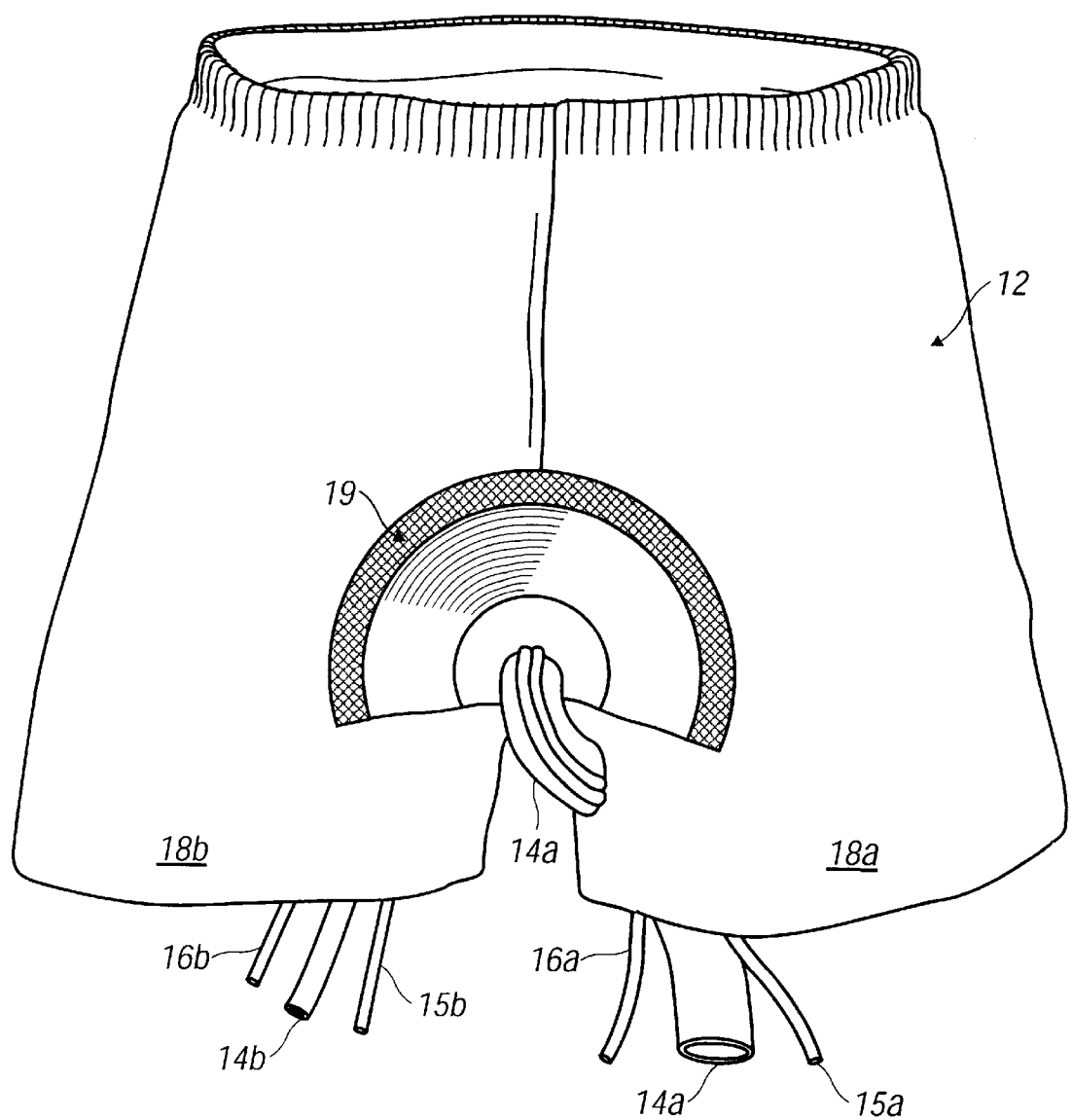
FIG. 4 is a rear perspective view of the specially adapted shorts 12 of the preferred embodiment of the present invention in which the relative size and placement of the provided solid waste collecting funnel 19 is highlighted.
Figure 5:
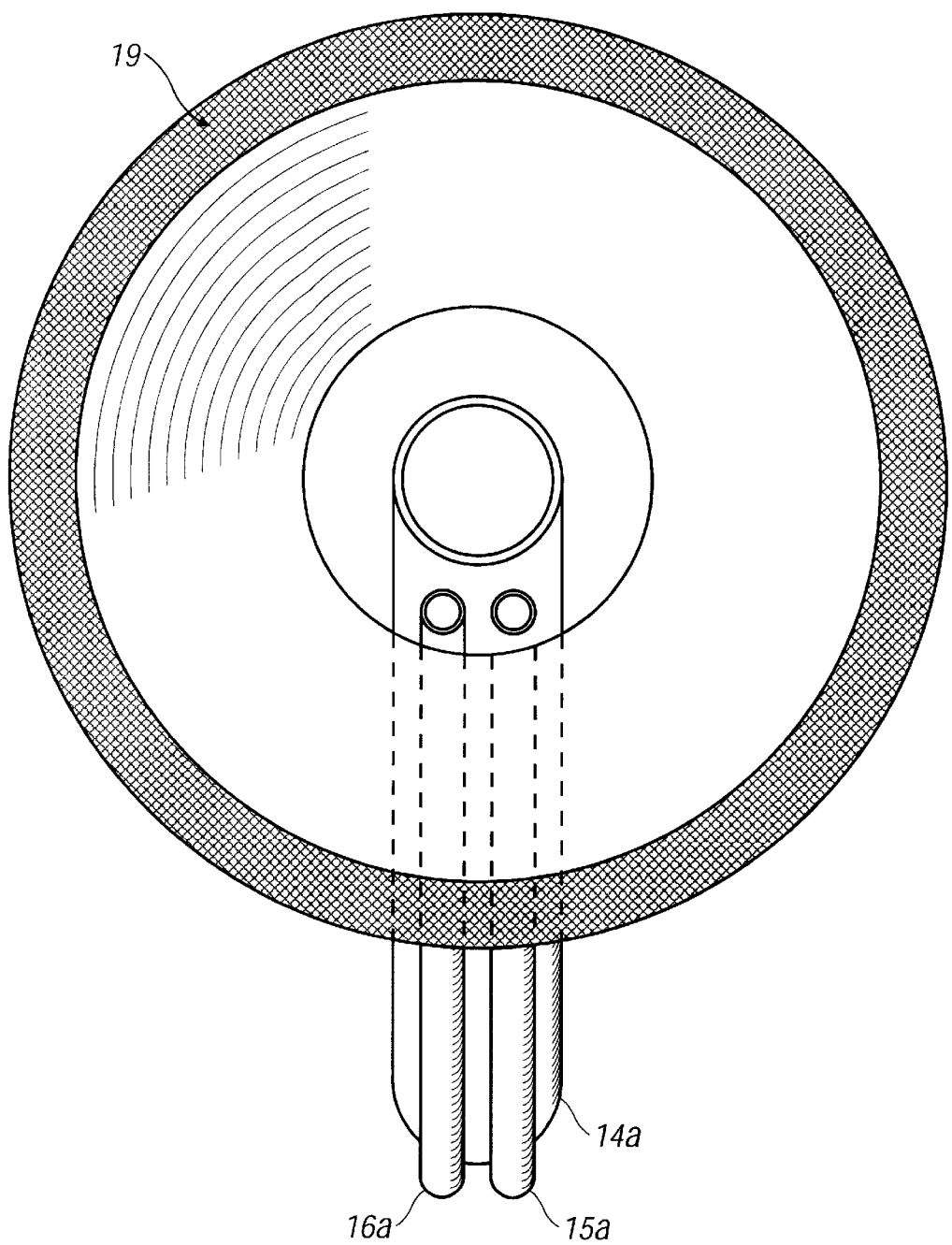
FIG. 5 is a plan view of the solid waste collecting funnel 19 of the preferred embodiment of the present invention.

Referring now to FIG. 2, the shorts 12 of the preferred embodiment 10 are shown in their open condition with the patient 11 absent. According to the preferred embodiment, the rectal area connecting tubes 14a, 15a, 16a are routed through the right short legging 18a and into the vertex of an oblately conic funnel 19 integrally provided in the rear of the shorts 12, and shown in detail in FIGS. 4 and 5. As will be apparent to those of ordinary skill in the relevant arts, the funnel 19, which preferably comprises a flexible, conformable material such as rubber, soft plastic or polyurethane, should be of sufficient size, and appropriately positioned, to completely encircle the patient's rectal area. The funnel 19 may be permanently or removably integrated into the rear area of the shorts 12. In order to promote patient comfort, it is desirable to manufacture the shorts 12 from a soft fabric such as cotton. In this case, the funnel 19 may be sewn in place, or removably affixed with releasably engagable hook and loop type material (such as that sold under the trademark VELCRO), zippering, or any other releasable closure means as is known to those of ordinary skill in the art.

While cotton fabric is preferred, those of ordinary skill in the art will recognize that other materials may be used with only a slight corresponding increase in manufacturing complexity. For example, the synthetic fiber material commonly known to those of ordinary skill in the art by the trademark LYCRA may be readily adapted for prolonged skin contact with no adverse effect. This material is commonly available as one ply bonded to a second ply of polyurethane material. Utilization of such a two-ply material for the shorts 12, allows the funnel 19 to then be RF-welded to the shorts 12, as is also well known to those of ordinary skill in the art of textile manufacturing.

At the genital area, connecting tubes 14b, 15b, 16b are routed through the left short legging 18b and into a bag, or pouch 20 provided adjacent the patient's genital area. This bag 20 is shown with a dotted line in FIG. 3, which depicts the shorts 12 of the preferred embodiment of the present invention in their closed condition. Routing the connecting tubes 14, 15, 16 through the short leggings 18 serves to stabilize the tubes 14, 15, 16 without the necessity for tape or bandaging which, as is known to those of ordinary skill in the art, can cause discomfort to the patient 11, requires the attention of the nursing staff, and generally increases the complexity of the tasks involved with patient care.

Notwithstanding these advantages to the preferred embodiment, however, those of ordinary skill in the art will readily recognize that there are many alternative embodiments available for the routing of the connecting tubes 14, 15, 16. Although such embodiments may result in corresponding loss of advantage, they are nonetheless considered within the scope of this present invention.

Figure 3:
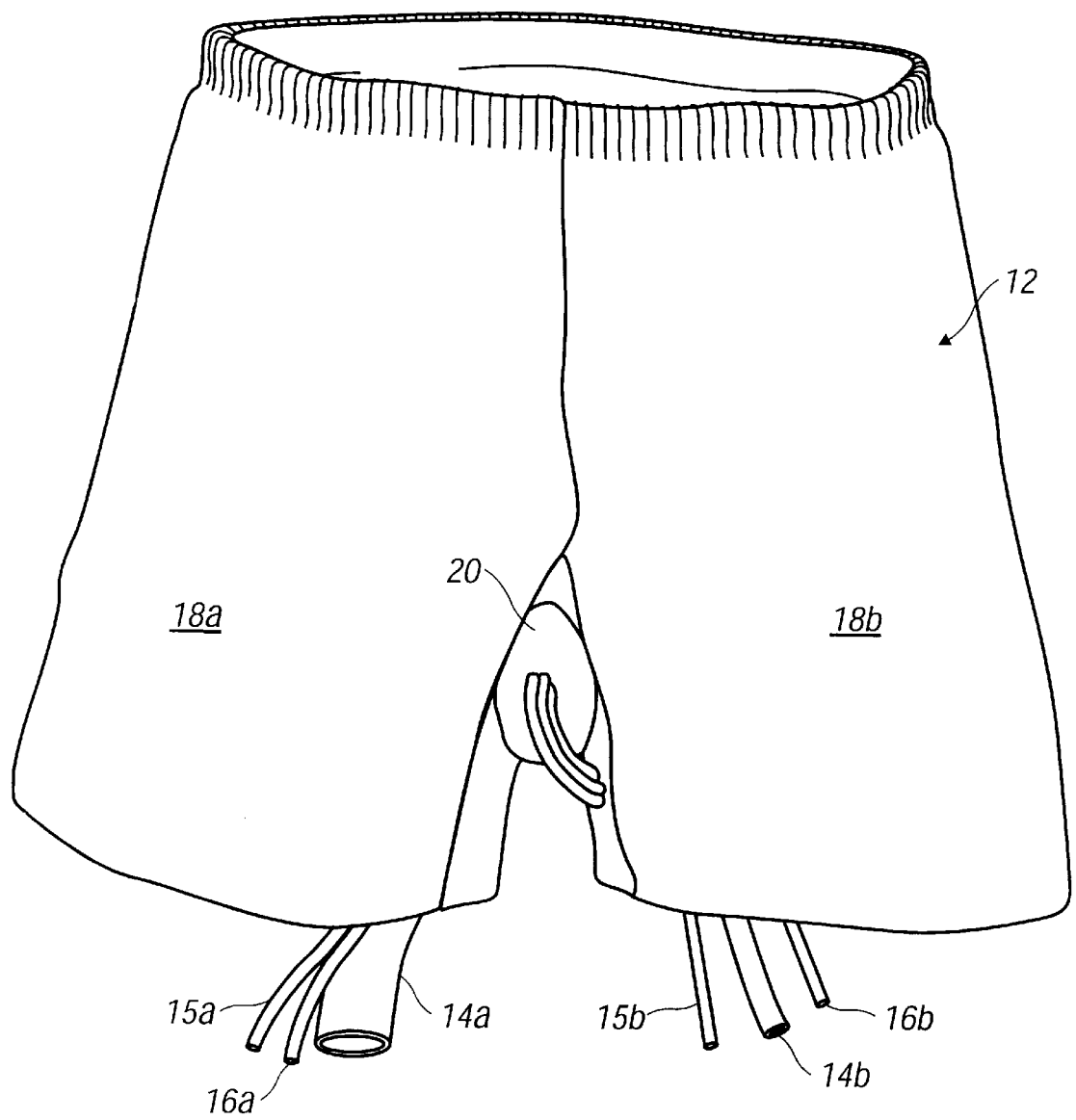
FIG. 3 is a front, perspective view of the specially adapted shorts 12 of the preferred embodiment of the present invention in their closed condition.

Referring particularly to FIGS. 2 and 3, the preferred means for affixing the shorts 12 to the patient 11 is detailed. Releasably engagable hook 21a and loop 21b type material, such as that known to those of ordinary skill in the art by the trademark VELCRO is utilized to promote easy application and adjustment of the shorts 12 upon the patient 11. The shorts 12 may be opened from top to bottom, allowing a diaper-like application as will be apparent to those of ordinary skill in the art. This method of attachment is particularly advantageous in that it allows a single sized short 12 to be applied patients within some range of body sizes. Application of the shorts 12 by this method is also very simple as is adjustment, whether the patient 11 be reclined or supine. It is noted that a simple extension of this invention, with only slight increase to the manufacturing complexity, is to make substantially all of the outer surface of the shorts 12 out of a hook-compatible pile-type material such that the shorts 12 are broadly adjustable for various patient sizes.

In the preferred embodiment of the present invention, sensors, as are known to those of ordinary skill in the relevant arts, are used to detect the excretion of urine or fecal matter by the patient 11. Upon the detection of one, the other or both, a vacuum extraction and cleansing cycle is initiated. In the first step, a vacuum pump is used to draw fecal matter into a fecal storage chamber 17a or urine into a urine storage chamber 17b, or both. The first step of this cycle should typically require about five minutes. In the second step, warmed cleansing fluid is pumped from a storage chamber 17c to either the patient's rectal or genital area, or both, depending on where waste was detected. The cleansing fluid is simultaneously evacuated from the patient area by the vacuum pump. This step will typically last for about one and a half minutes. In a final step, warmed air is distributed upon the patient's 11 skin from a source within the base 22 of the collection unit 13. This allows the patient 11 to be quickly dried with a minimum of discomfort. This should typically require only about one minute. The entire operating cycle is preferably under the control of a microprocessor based system, although those of ordinary skill in the art will recognize many alternative methods such as simple state machines or electro-mechanical control devices, as well as manual initiation and operation.

It is noted that the fecal and urinary wastes are delivered to separate storage chambers 17a, 17b which are removable for convenient cleaning and may be provided with closure means in order to prevent odors from escaping into the surrounding environment. This configuration allows the attending care givers separate access to the fecal and urinary matter for laboratory testing with minimum infringement into the patient's comfort and privacy. This method also allows the care giver to separately measure the patient's urinary and bowel outputs. Those of ordinary skill in the art will readily recognize that many extensions may be made in this area within the scope of this present invention. For example, the cleaning fluid may be evacuated to a fourth chamber 17 in order to prevent contamination or dilution of the sample material or measuring marks may be added to the chamber surfaces or scales may be integrated into the unit 13.

Finally, the present invention 10 is provided with an appropriate power source, which is alternatively self contained and portable in order to allow maximum utilization in a variety of institutional, residential and even outdoor settings. In one embodiment, the system is battery based thereby allowing the patient to be moved within the hospital or home while the evacuation system 10 remains in place. The preferred embodiment also comprises a second power supply adapted for use with standard wall outlets in order to preserve battery strength when such facilities are available.

While the description given herein reflects the best mode known to the inventor, those of ordinary skill in the relevant arts will quickly recognize that there are endlessly many alternate embodiments of the teachings herein. Exemplary of such extensions as may be made of these teachings, those of ordinary skill in the relevant arts will see that the apparatus and methods herein disclosed are readily extendible to a vacuum extraction system integrated within a hospital bed. Recognizing that those of ordinary skill in the art will easily see such alternate embodiments and extensions in application, they have in most cases not been detailed in order to preserve clarity.

A waste evacuation system and its components have been described herein. These and other variations, which will be appreciated by those skilled in the art, are within the intended scope of this invention as claimed below. As previously stated, detailed embodiments of the present invention are disclosed herein; however, it is to be understood that the disclosed embodiments are merely exemplary of the invention that may be embodied in various forms.

What is claimed is:

1. A method for maintaining a sanitary environment about a bedridden patient, said method comprising the steps of:
   automatically detecting the presence of bodily waste excreted by the patient;
   diverting detected bodily waste from the patient in automated response to the detection thereof and utilizing a waste removal system adapted to separately divert solid and liquid waste from the patient;
   collecting and maintaining the solid and liquid waste removed away from the patient in substantially separate compartments; and
   cleansing the patient of remnant bodily wastes after said diverting step.

2. The method as recited in claim 1, wherein said diverting step comprises automatically activating a waste removal system.

3. The method as recited in claim 1, wherein said cleansing step comprises:
   providing a cleansing fluid to said area adjacent the patient's body; and
   providing a drying fluid to said area adjacent the patient's body.

4. The method as recited in claim 3, wherein:
   said providing a cleansing fluid step comprises supplying a liquid cleanser; and
   said providing a drying fluid step comprises supplying heated air.

5. The method as recited in claim 1, wherein said waste removal system further comprises:
   a garment adapted for collecting bodily waste from said area adjacent the patient's body; and
   a collection and storage unit in fluid communication with said garment.

6. The method as recited in claim 5, wherein said garment comprises a pair of shorts having integrated therein a funnel for collecting bodily waste.

7. The method as recited in claim 5, wherein said funnel is adapted for the separate collection of solid waste from the patient's rectal area.

8. The method as recited in claim 5, wherein said funnel is adapted for the separate collection of liquid waste from the patient's genital area.

9. The method as recited in claim 5, wherein said shorts comprise releasably engageable hook and loop fasteners for removably affixing said shorts to the patient.

10. The method as recited in claim 6, wherein said shorts comprise a polyurethane laminate.

11. The method as recited in claim 10, wherein said funnel is RF-welded to said polyurethane laminate.

12. The method as recited in claim 6, wherein said collection and storage unit comprises:

a plurality of chambers for the separate collection and storage of solid waste, liquid waste, cleansing fluid and drying fluid.

13. The method as recited in claim 12, wherein said chambers are removably engageable with said collection and storage unit.

14. The method as recited in claim 12, wherein said collection and storage unit further comprises a controller.

15. The method as recited claim 14, wherein said controller comprises a microprocessor based control system.

16. The method as recited in claim 14, wherein said controller is adapted to initiate said diverting step in response to detection in said detecting step of the presence of bodily waste excreted by the patient.

17. The method as recited in claim 16, wherein said controller is further adapted to initiate said cleansing step at a time following initiation of said diverting step.

18. A waste evacuation system for maintaining a sanitary environment about a bedridden patient comprising:

a garment adapted for collecting bodily waste from an area adjacent a patient's body;

a collection and storage unit in fluid communication with said garment, said storage unit comprising a plurality of chambers for the separate collection and storage of solid waste and liquid waste and storage of cleansing fluid;

a sensor for detecting the excretion of urine or fecal matter;

a vacuum pump in fluid communication with the area adjacent the patient's body;

a means for supplying a liquid cleanser to the patient's body;

a means for supplying drying air to the patient's body; and a means for heating the liquid cleanser and drying air.

19. The waste evacuation system as recited in claim 18, further comprising a powering system.

20. The waste evacuation system as recited in claim 19, wherein said powering system is a battery pack.

21. The waste collection system as recited in claim 18, wherein said garment comprises a pair of shorts having integrated therein a funnel for collecting bodily waste.

22. The waste collection system as recited in claim 21, wherein said funnel is adapted for the separate collection of solid waste from the patient's rectal area.

23. The waste collection system as recited in claim 21, wherein said funnel is adapted for the separate collection of liquid waste from the patient's genital area.

24. The waste collection system as recited in claim 21, wherein said shorts comprise:

releasably engageable hook and loop fasteners for removably affixing said shorts to the patient.

25. The waste collection system as recited in claim 21, wherein said shorts comprise:

a polyurethane laminate.

26. The waste collection system as recited in claim 25, wherein said funnel is RF-welded to said polyurethane laminate.

27. The waste collection system as recited in claim 18, wherein said collection and storage unit comprises a plurality of chambers.

28. The waste collection system as recited in claim 27, wherein said chambers are removably engageable with said collection and storage unit.

29. The waste collection system as recited in claim 18, wherein said collection and storage unit further comprises:

a controller.

30. The waste collection system as recited in claim 29, wherein said controller comprises:

a microprocessor based control system.

31. The waste collection system as recited in claim 29, wherein said controller is adapted to initiate said diverting step in response to detection in said detecting step of the presence of bodily waste excreted by the patient.

32. The waste collection system as recited in claim 31, wherein said controller is further adapted to initiate said cleansing step at a time following initiation of said diverting step.

33. A method for maintaining a sanitary environment about a patient, said method comprising the steps of:

automatically detecting the presence of bodily waste excreted by the patient utilizing an automatic detection device free from care-giver initiation;

diverting detected bodily waste from the patient in automated response to the detection thereof utilizing a waste removal system adapted to separately divert solid and liquid waste from the patient; and cleansing the patient of remnant bodily wastes after said diverting step.

34. A method for maintaining a sanitary environment about a patient, said method comprising the steps of:

automatically detecting the presence of bodily waste excreted by the patient utilizing an automatic detection device free from care-giver initiation; and diverting detected bodily waste from the patient in automated response to the detection thereof utilizing a waste removal system adapted to separately divert solid and liquid waste from the patient.

35. The method as recited in claim 34, said method further comprising:

collecting and maintaining the solid and liquid waste removed away from the patient in substantially separate compartments.

* * * * *